United States Patent
Lepage (10) Patent No.: US 8,704,513 B2
(45) Date of Patent: Apr. 22, 2014

(54) SHIELDED EDDY CURRENT COILS AND METHODS FOR FORMING SAME ON PRINTED CIRCUIT BOARDS

(75) Inventor: Benoit Lepage, Quebec (CA)

(73) Assignee: Olympus NDT Inc., Waltham, MA (US)

( * ) Notice: Subject to any disclaimer, the term of this patent is extended or adjusted under 35 U.S.C. 154(b) by 359 days.

(21) Appl. No.: 13/028,519

(22) Filed: Feb. 16, 2011

(65) Prior Publication Data

US 2012/0206132 A1    Aug. 16, 2012

(51) Int. Cl.
    *G01R 33/12* (2006.01)

(52) U.S. Cl.
    USPC ......................................................... 324/239

(58) Field of Classification Search
    USPC ......................................................... 324/239
    See application file for complete search history.

(56) References Cited

U.S. PATENT DOCUMENTS

| | | | |
|---|---|---|---|
| 5,293,119 A | 3/1994 | Podney | |
| 5,389,876 A * | 2/1995 | Hedengren et al. | 324/242 |
| 5,659,248 A | 8/1997 | Hedengren et al. | |
| 7,528,598 B2 * | 5/2009 | Goldfine et al. | 324/240 |
| 7,626,383 B1 * | 12/2009 | Sun et al. | 324/240 |
| 2001/0054896 A1 * | 12/2001 | Mednikov et al. | 324/225 |
| 2008/0204118 A1 * | 8/2008 | Kuhn | 327/517 |
| 2012/0007595 A1 * | 1/2012 | Lepage | 324/239 |

FOREIGN PATENT DOCUMENTS

DE    10 2007 027 822    12/2008

OTHER PUBLICATIONS

Office Action issued by the German Patent Office on Jan. 2, 2013 in connection with corresponding application No. DE10 2011 104 296.6 and partial English translation thereof.

* cited by examiner

*Primary Examiner* — Bot Ledynh
(74) *Attorney, Agent, or Firm* — Ostrolenk Faber LLP (57) ABSTRACT

A shielded eddy current coil probe is formed on a printed circuit board and comprises a first coil component forming a test coil and a second coil component forming an active shielding coil. The test coil and the active shielding coil are concentrically arranged and the number of coil windings in the active shielding coil and the field direction thereof are configured to limit the induced field or the sensed field in the test object to the footprint area of the test coil on the test object. Multiple sets of test coils with active shielding coils can be provided on the same or different layers of the printed circuit board to realize different driver, receiver and combined driver/receiver coil configurations.

19 Claims, 6 Drawing Sheets

SHIELDED EDDY CURRENT COILS AND METHODS FOR FORMING SAME ON PRINTED CIRCUIT BOARDS

FIELD OF THE INVENTION

The present invention relates to non-destructive object testing and inspection systems (NDT/NDI), using Eddy Current Testing (ECT) and, more particularly, to Eddy Current (EC) probes etched on printed circuit boards (PCB) which are shielded to concentrate the generated fields onto the testing location.

BACKGROUND OF THE INVENTION

ECT inspection is commonly used in NDT/NDI applications to detect flaws in surfaces of manufactured components fabricated out of conductive materials, such as steel bars, tubes and pipes. ECT is often used to inspect components for automotive, aeronautic and energy industries. Over the years, ECT sensors have been designed with different configurations and patterns to suit for different applications.

Various ECT systems have heretofore been provided for the detection of cracks and or other flaws in a part under test. In general, such systems include field producing means such as a coil connected to an AC source to generate Eddy currents in a part and a sensing means to sense the field produced by the Eddy currents. The sensing means may be a separate coil, a Hall probe, or any other field responsive device, or the coil of the field-producing means may also be used to sense the EC-induced field, by measuring the effective impedance thereof.

One of the challenges of performing an ECT inspection is getting sufficient eddy current field strength in the region of interest within the material. Another challenge is keeping the field away from nonrelevant features of the test component. The impedance change caused by nonrelevant features can complicate the interpretation of the signal. Probe shielding and loading are sometimes used to limit the spread and concentrate the magnetic field of the coil. Of course, if the magnetic field is concentrated near the coil, the eddy currents will also be concentrated in this area.

Eddy current probes are most often shielded using magnetic shielding or eddy current shielding. Magnetically shielded probes have their coil surrounded by a ring of ferrite or other material with high permeability and low conductivity. The ferrite creates an area of low magnetic reluctance and the probe's magnetic field is concentrated in this area rather than spreading beyond the shielding. This concentrates the magnetic field into a tighter area around the coil.

Eddy current shielding uses a ring of highly conductive but nonmagnetic material, usually copper, to surround the coil. The portion of the coil's magnetic field that cuts across the shielding will generate eddy currents in the shielding material rather than in the nonrelevant features outside of the shielded area. The higher the frequency of the current used to drive the probe, the more effective the shielding will be due to the skin effect in the shielding material.

While the shielding methods mentioned above are suitable solutions for conventional eddy current coils, they are not adapted for coils built on printed circuit boards. In this case, a magnetic shield is not compatible with the manufacturing processes. As for the conductive shield, its effectiveness would be strongly tied to test frequency because copper layers on printed circuit boards are typically very thin (in general approximately 18 micrometer thick for a flexible printed circuit board with finely etched traces). Considering the depth of penetration of the eddy currents, such thin shield would limit the use of the probe to very high frequencies such as 10 MHz and more.

Another limitation of conventional shields is the inability to overlap shielded coils over the same physical position, thus limiting the available coils configurations. Even if the conventional shields were made very thin, it would not be possible to successfully stack them because the shield of a first coil would interact with a second overlapped shielded coil in such way that none of these coils will operate properly.

Yet another limitation of conventional shield is their inability to operate properly at DC or very low frequency, such as required for remote field (RFT) or magnetic flux leakage (MFL) test methods

SUMMARY OF THE INVENTION

Accordingly, it is an object of the present invention to provide a method for limiting the spread of the magnetic field generated by an eddy current coil etched on a printed circuit board.

It is a further object of the invention to provide shielding performances over a broad frequency range.

It is also an object of the invention that this solution be fully integrated in the PCB itself so that cost and flexibility of the probe will not be affected.

A further object of the invention is for this solution to be suitable for multiple eddy current coil configurations such as absolute and transmit-receive configurations.

Yet another object of the invention is for this solution to be suitable for providing shielding outside and/or inside the coil on which this solution is applied.

A still further object of the invention is for this solution to make it possible to overlap several layers of shielded coils over the same physical position.

The forgoing and other objects of the inventions are realized in PCB implementations of EC probes that restrain the interaction of an eddy current testing (ECT) coil inside and/or outside the coil radius without using ferromagnetic material or thick conductive layers of material. The invention makes it possible to shield coils etched on printed circuit board and operate them over a wide frequency range.

In accordance with one preferred embodiment of the invention, these objectives are attained by providing an additional active shielding coil with the test coil of an EC probe formed on a PCB. The field magnitude generated by the active shielding coil is set to null the field(s) generated by the test coil at a field nulling line, which is located outside the desired test coil(s) sensing area. Field nulling is accomplished by injecting a current that has the same frequency, but opposite phase to that of the test coil current. This can be accomplished by having a single coil, with an initial winding that forms the test coil and a further winding, connected in series but reversed in direction for the remainder of the winding, whereby the reverse direction coil creates the nulling field.

In accordance with an embodiment of the invention, the eddy current probe comprises a printed circuit board with a first coil component and second coil component formed thereon. The first coil component is a test coil formed on the circuit board and the second coil component is an active shielding coil with the test coil and the active shielding coil being concentrically arranged. The active shielding coil is driven with a drive signal which is set to limit the field induced within a test object against which the eddy current probe is placed and/or limit detection of eddy current fields in the test object, to an area substantially coextensive with an area over which the test coil extends on the test object. Preferably, the test coil and the active shielding coil are connected in series with one another, but the active shielding coil is wound in a direction opposite to that of the test coil winding. The eddy current probe can be operated as a drive coil and/or as a receiver coil. Multiple sets of coils can be formed on the printed circuit board in various overlapping and concentrically arranged or laterally offset configurations, to form single probes or an array of probes.

Other features can be attained by combining the benefits of shielded eddy current coils and flexible printed circuit board manufacturing methods. These benefits include a fully automated, low cost reproducible process, mechanical flexibility and an ability to provide very thin probes that allow inspection in tight areas. The invention further facilitates providing shielding performance over a broad frequency range, from DC to at least 25 MHz ranges. Lastly, the ability to add several layers of independently shielded coils over the same physical position, while allowing these overlapping coils to be part of the same assembly (i.e. transmit and receive coils) or part of different sensor assemblies of the eddy current probe, constitutes further advantageous of the invention.

Other features and advantages of the present invention will become apparent from the following description of the invention which refers to the accompanying drawings.

DETAILED DESCRIPTION OF THE INVENTION

Referring to FIGS. 1A, 1B, 2A and 2B, in order to conduct an ECT inspection, a thin test coil 1 is positioned in close proximity to an electrically conductive component 2, which constitutes the test object. The test coil 1 depicted here is 18 μm thick, which is representative of the thickness that can be obtained for coils etched on flexible printed circuit boards. AC current 9 flows in the test coil 1 to generate an alternating magnetic field at the same frequency. Eddy currents opposing this magnetic field are then induced in the conductive, test component 2 located underneath the test coil 1.

Figure 1A:
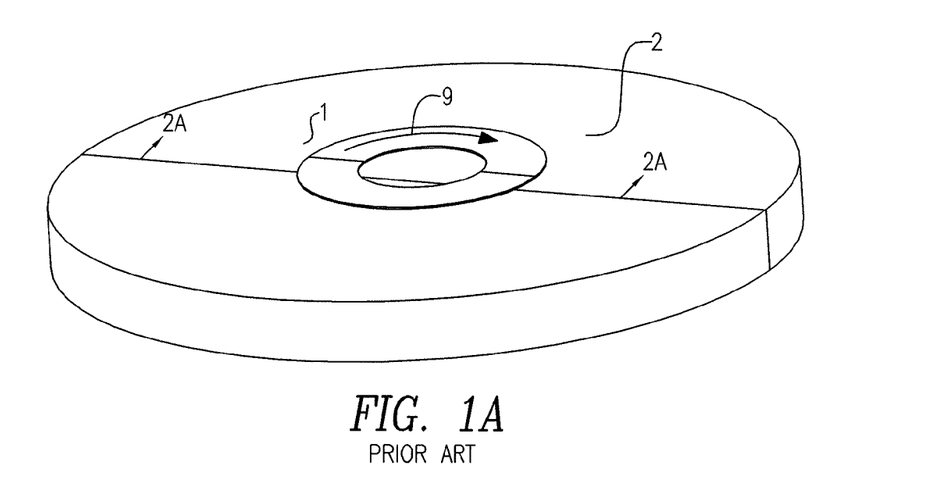
FIG. 1A shows an isometric view of a 18 μm thick, 2 mm OD prior art coil over a conductive component.
Figure 1B:
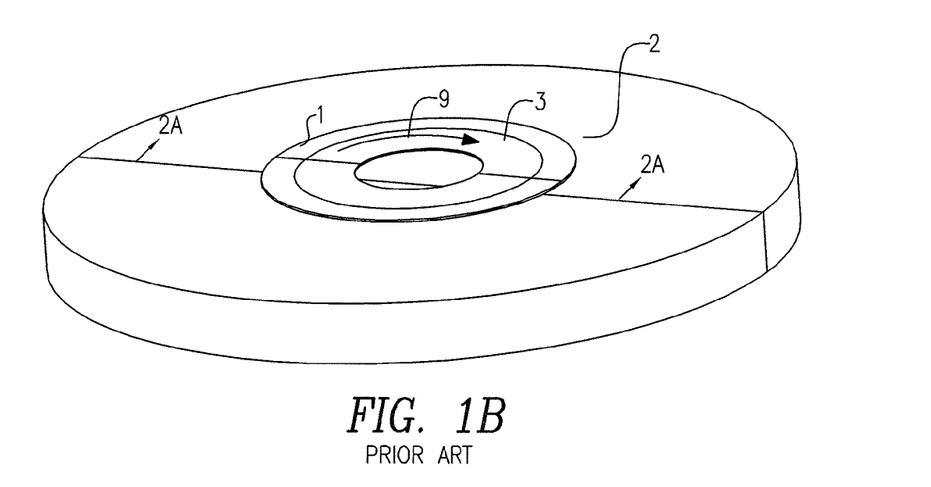
FIG. 1B shows an isometric view of a 18 μm thick, 2 mm OD prior art coil surrounded by a 0.5 mm large eddy current shield over a conductive component.
Figure 2A:
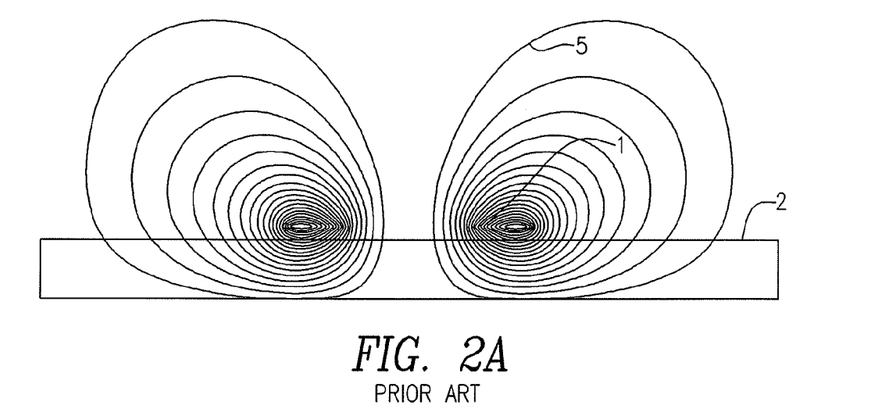
FIG. 2A shows the magnetic field lines generated by FIG. 1A coil at 5 kHz test frequency
Figure 2B:
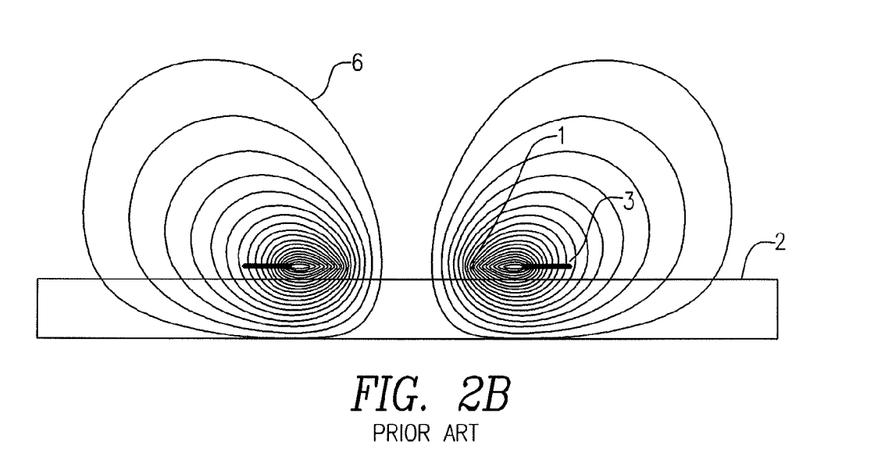
FIG. 2B shows the magnetic field lines generated by FIG. 1B coil at 5 kHz test frequency

FIG. 2A illustrates a magnetic field lines distribution 5 for the non-shielded test coil 1 shown on FIG. 1A using a 5 kHz test frequency. As illustrated in FIG. 2A, the magnetic field spreads over a considerable width (area) in the test component 2, thus inducing eddy currents over an area much larger than the footprint of the test coil 1.

In order to use the test coil 1 near important geometrical features such as part edges or fasteners, it is desirable to restrain the spread of the magnetic field to the test coil 1 footprint. A prior art means for accomplishing this is to use a conductive ring 3, concentric with the test coil 1. While this method has proven itself to be effective for relatively thick test coils, it can be seen in FIG. 2B that for a thin conductive ring 3 such as those etched on a printed circuit board, the magnetic field line distribution 6 still spreads within the test part over a much larger area than the test coil 1 footprint.

Figure 3A:
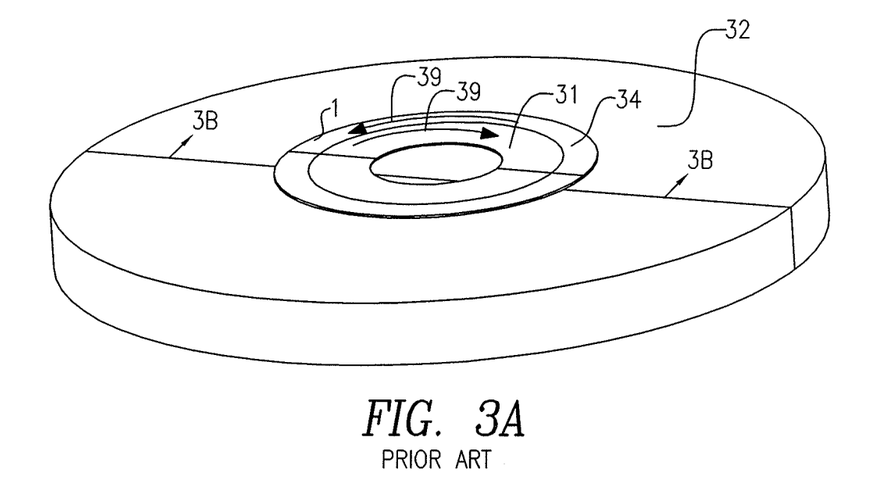
FIG. 3A shows an isometric view of a 18 μm thick, 2 mm OD coil surrounded by a 0.5 mm large active shield, built using the teaching of the invention, over a conductive component.
Figure 3B:
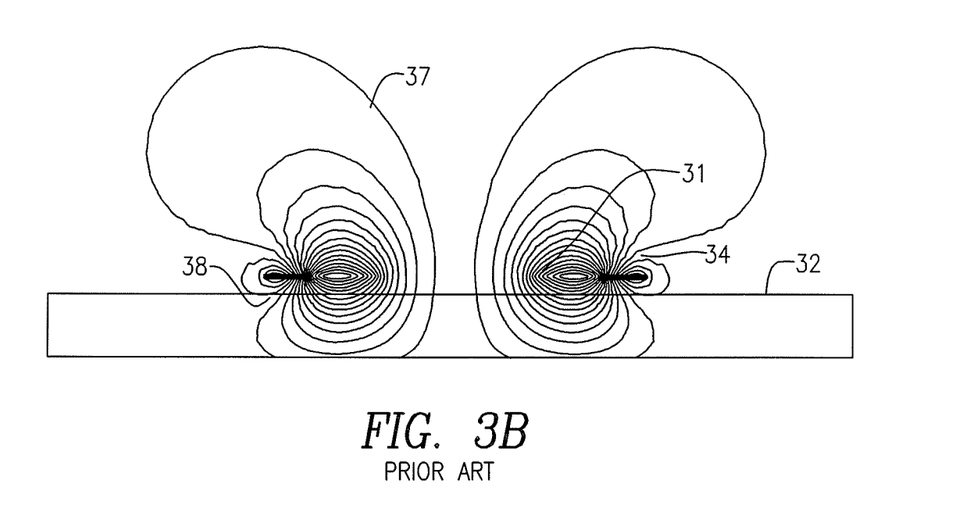
FIG. 3B shows the magnetic field lines generated by FIG. 3A coil at 5 kHz test frequency FIG. 4A show a spiral coil structure built using the teaching of the invention

The proposed means to provide an effective shielding for very thin coil is illustrated in FIG. 3A. The idea is to actively generate a magnetic field using an active shielding coil 34 concentric to the test coil 31. The field magnitude generated by the active shielding coil 34 is set to null the field generated by the test coil 31 at a field nulling region 38 (FIG. 3B), which is located out of the desired test coil's sensing area. Such field nulling is accomplished by injecting a current 30 that is at the same frequency but opposite in phase to the test coil current 39. FIG. 3B illustrates the magnetic field lines generated by a circular test coil 31 and a properly set shielding coil 34.

It is well known that magnetic field magnitudes generated by a coil are proportional to N*I, namely, the number of turns (N) times the current (I). Thus, it is possible to reach the desired field magnitude for the active shield coil 34 either by adjusting the current I or by adjusting the number of turns N in the active shield coil 34. It is also interesting to note that the ratio [N(31)*I(31)]/[N(34)*I(34)] (where "31" and "34" refer to coil 31 and coil 34, respectively), required to provide shielding at nulling location 38 is independent of the test frequency, provided that the electromagnetic field reflected by the inspected part is small compared to the primary field. Therefore, once a fixed [N(31)*I(31)]/[N(34)*I(34)] ratio is established, the actively shielded coil can effectively be used over a broad frequency range.

Figure 4A:
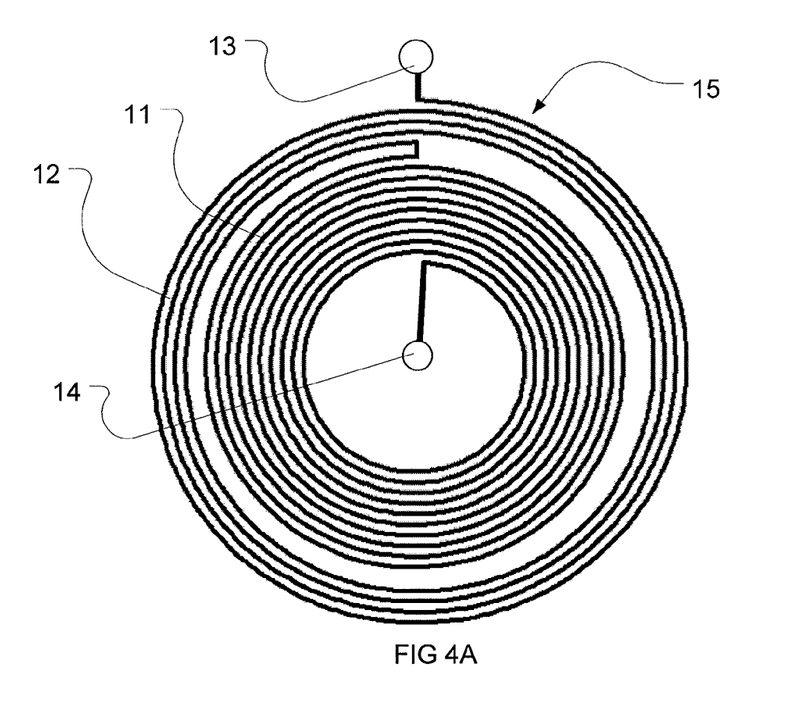

Coils manufactured on printed circuit boards are typically spiral shaped. Thus, as seen in FIG. 4A, by providing a clockwise wound, spiral shaped test coil 11 and a counter-clockwise wound, spiral shape active shield 12 connected in series, it is possible to obtain an actively shielded coil assembly 15 that fully integrates both components. For the 2 mm OD (outer diameter) test coil 11, the optimal ratio between the test coil 11 and active shield coil 12 is approximately 10/3. Optimal turn ratios can be precisely evaluated using commercially available magnetic field simulation software. The coil 15 is connected through the PCB assembly using contacts 13 and 14 or by soldering wires on contacts 13 and 14.

Although the drawings describe the test coil 11 and the active shield coil 12 to be connected in series with the active shield coil 12 being wound oppositely to the test coil, in accordance with another embodiment, the coils may be wound in the same direction. In such an embodiment, the active shield coil would be simply provided electronically with a drive signal which is 180° out of phase with the drive signal for the test coil. This arrangement also allows setting the magnitude of the drive signal for the active shield coil during a calibration process to optimize the response.

Figure 4B:
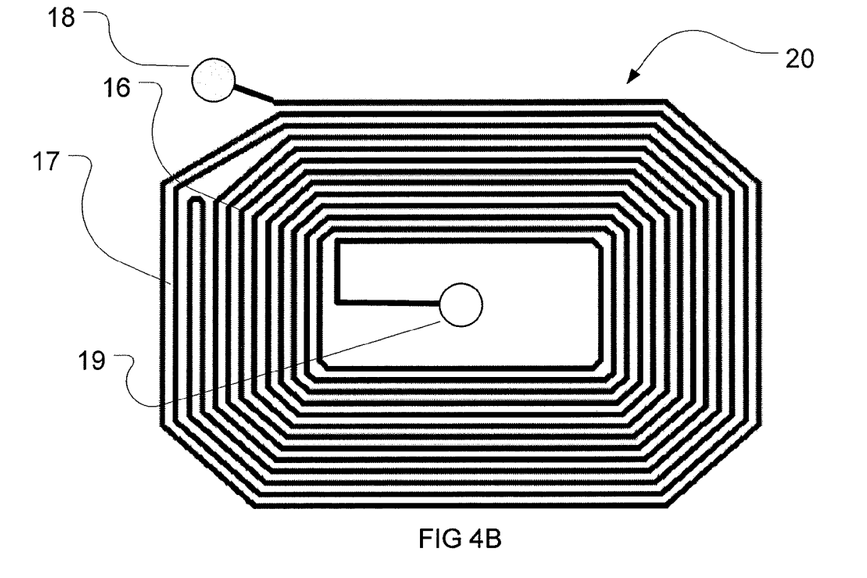
FIG. 4B shows a rectangular coil structure built using the teaching of the invention

Using the same principles, various coils shapes can be produced. An actively shielded rectangular shaped coil 20, shown in FIG. 4B, includes a test coil 16 and an active shield 17. The coil assembly 20 is interesting in this case because, unlike coil 15, the distance between the test coil and shielding coil is nearly constant, providing better test results uniformity.

Figure 5A:
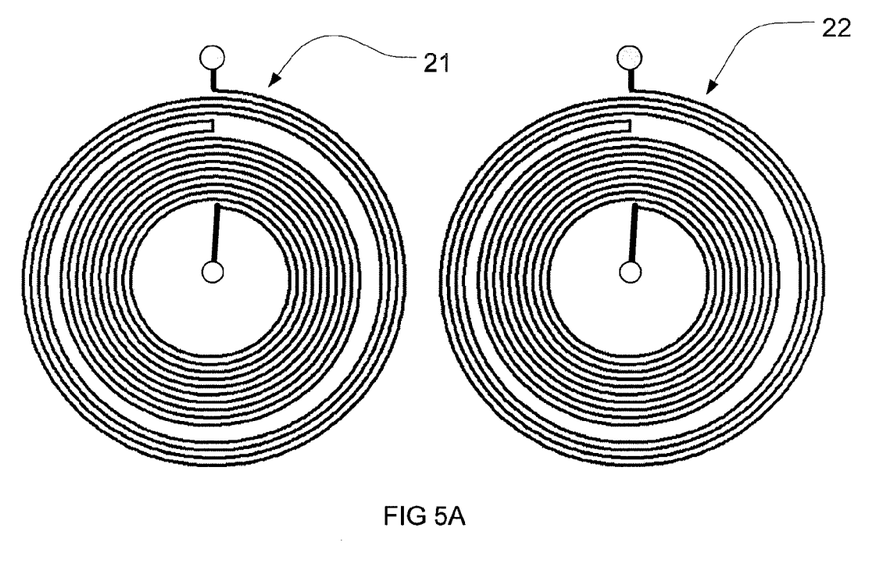
FIG. 5A shows the possible use of the invention in the transmit receive configuration

Another important aspect of the invention is the use of actively shielded coil spirals such as 15 and 20 as receiver coils. In this case, the objective of shielding is to become insensitive to eddy currents flowing outside the coil's footprint. The Lorentz electromagnetic reciprocity principle states that the relationship between an oscillating current and the resulting electric field is unchanged if one interchanges the points where the current is placed and where the field is measured. For the invention, it means that if a coil configuration of FIG. 5A provides adequate shielding for a driver coil 21, it will also provide adequate shielding for its use as a receiver 22. FIG. 5A illustrates a shielded transmit receive coil configuration using the teachings of the invention.

Figure 5B:
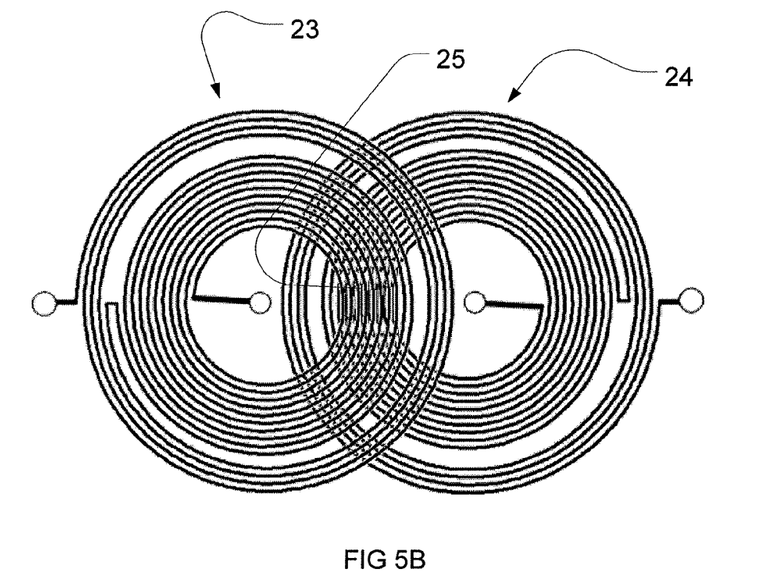
FIG. 5B shows the possible use of the invention on a multilayer structure where multiple coils overlap over the same physical position.

Yet another interesting aspect of the actively shielded coil spirals is that they allow magnetic fields to pass through without perturbation. This unique feature allows multiple actively shielded coils to be superposed, as illustrated on FIG. 5B. In this example, an actively shielded driver coil 23 is etched on a first PCB layer while an actively shielded receiver coil 24 is etched on a second PCB layer. A highly sensitive zone 25 is thus created at the intersection of both coils since both coils directly interact only in this area. This feature also allows the use of multiple overlapping actively shielded coils as part of an eddy array probe.

Figure 6A:
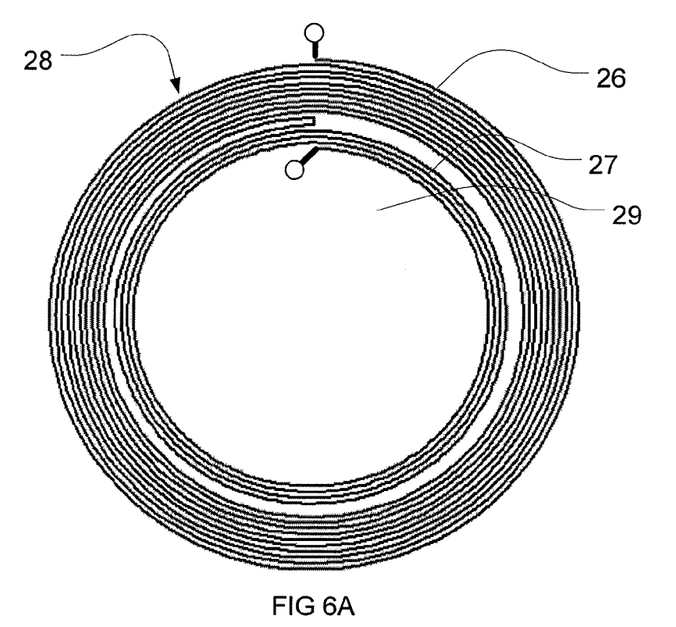
FIG. 6A shows an alternate configuration based on the teaching of this invention that provides internal shielding
Figure 6B:
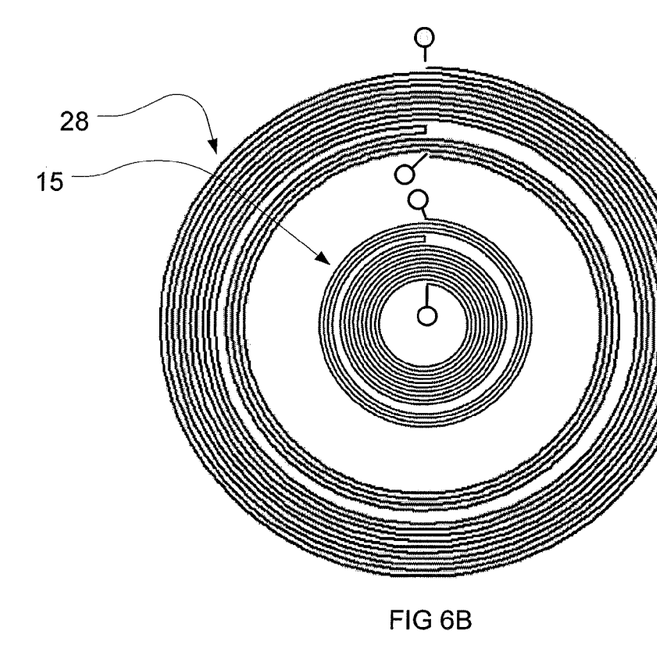
FIG. 6B shows the combined use of internal and external shielding to build a coil with test results equivalent to those of the coil structure described in U.S. Pat. No. 5,617,024.

Another embodiment of the invention comprises using the active shield to shield inside the test coil, as illustrated in FIG. 6A. In this case, an active shield coil 27 is located concentrically inside a test coil 26 to provide an internally shielded coil assembly 28. The number of turns of the active shield coil is set to null the resulting magnetic field at field nulling location 29. An example of use for such configuration is pictured in FIG. 6B. In this case, the internally shielded driver coil assembly and externally shielded coil assembly 15 are configured to reproduce the sensor described in U.S. Pat. No. 5,617,024, the teachings of which are incorporated by reference herein.

As described above, the inventions herein realize:
  Active shielding for eddy current test coils and or driver coils by using a set of concentric coils to limit the spreading of the magnetic field under an eddy current test coil which test coil is suitable for or at:
    Any test frequency from DC to 25 MHz;
    Coils being etched on printed circuit boards;
    Various coil shapes such as round, rectangular, etc; and
    External or internal shielding.
  Active shielding for eddy current receiver coils by using a set of concentric coils to limit the sensing area of the receiver coil to be used for eddy current testing.
  Probe configurations where multiple actively shielded coils can overlap over the same physical position without mutual interaction, enabling providing coils for the case where a transmit receive configuration with high sensitivity zone is needed and/or the case of an array probe with channels overlapping on a multiple PCB layers.
  Usage for other electromagnetic techniques such as remote field and magnetic flux leakage, taking advantages of their low frequency performances.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

The invention claimed is:

1. An eddy current probe, comprising:
  a printed circuit board; and
  a first coil component comprising a test coil formed on the printed circuit board and a second coil component comprising an active shielding coil formed on the printed circuit board, wherein the test coil and the active shielding coil are concentrically arranged and wherein the coil windings in the active shielding coil are set to limit a field induced within a test object against which the eddy current probe is placed or limit detection of eddy current fields in the test object to an area substantially coextensive with an area over which the test coil extends on the test object, wherein the test coil and the shielding coil are constituted of a single winding, and wherein a winding direction of the shielding coil is opposite to a winding direction of the test coil.

2. The eddy current probe of claim 1, wherein the first coil component is configured to operate as a driver coil which induces eddy currents in the test object.

3. The eddy current probe of claim 1, wherein the first coil component is configured to operate as an eddy current receiver coil designed to sense eddy currents flowing in the test object.

4. An eddy current probe, comprising:
  a printed circuit board; and
  a first coil set and a second coil set wherein the first coil set and the second coil set located at a different layer of the printed circuit board and overlapping one another at a particular area of the printed circuit board, and wherein the first coil set and the second coil set each respectively further comprising,
  a respective first coil component comprising a test coil formed on the printed circuit board and a respective second coil component comprising an active shielding coil formed on the printed circuit board, wherein the test coil and the active shielding coil are concentrically arranged and wherein the coil windings in the active shielding coil are set to limit a field induced within a test object against which the eddy current probe is placed or limit detection of eddy current fields in the test object to an area substantially coextensive with an area over which the test coil extends on the test object, wherein the test coil and the shielding coil are constituted of a single winding, and wherein a winding direction of the shielding coil is opposite to a winding direction of the test coil.

5. The eddy current probe of claim 1, wherein the shielding coil surrounds the test coil.

6. The eddy current probe of claim 1, wherein the shielding coil is located inside the test coil.

7. The eddy current probe of claim 1, wherein the test coil and the shielding coil have generally circular configurations.

8. The eddy current probe of claim 1, wherein the test coil and the shielding coil have generally rectangular configurations.

9. The eddy current probe of claim 1, wherein the eddy current probe comprises at least two concentrically arranged probe systems, with a first probe system comprising said test coil and said shielding coil surrounding said test coil and a second probe system arranged around said first probe system and comprising an outer coil set comprising a secondary test coil and a secondary shielding coil.

10. The eddy current probe of claim 9, wherein the secondary test coil surrounds the secondary shielding coil.

11. The eddy current probe of claim 1, further including a plurality of coil sets, each coil set including a respective test coil and an associated shielding coil, the probe being configured as an array probe.

12. The eddy current probe of claim 1, wherein the number of windings in the shielding coil is effective to limit the induced field or the detection of the eddy current fields.

13. The eddy current probe of claim 1, wherein the eddy current probe comprises at least a first probe system and a second probe system, the first probe system comprising said test coil and said active shielding coil, said second probe system comprising a secondary test coil and a secondary shielding coil, said first and second probe systems being located on different layers of the PC board and being arranged to partially overlap one another to create a more sensitive area of field detection in an overlapped portion of said first and second probe systems.

14. The eddy current probe of claim 1, wherein said test coil is driven with a signal of a predetermined waveform and wherein said active shielding coil is driven with a signal which is 180° out of phase relative to said drive signal.

15. The eddy current probe of claim 1, wherein the probe is operable at frequencies from near zero to 25 MHz.

16. The eddy current probe of claim 4, wherein the first coil set is configured as a driver coil and the second coil set is configured as a receiver coil.

17. The eddy current probe of claim 1, wherein the probe is configured as a remote field device.

18. The eddy current probe of claim 1, wherein the probe is configured as a magnetic flux leakage detection device.

19. The eddy current probe of claim 1, wherein the printed circuit board is formed to be flexible, so as to allow its shape to conform to a surface shape of the test object.

* * * * *